US006571601B2

(12) United States Patent
Irion et al.

(10) Patent No.: US 6,571,601 B2
(45) Date of Patent: Jun. 3, 2003

(54) METHOD FOR DETERMINING THE REDUCING AGENT CONCENTRATION ($NH_3$) IN THE EXHAUST-GAS FLOW OF AN INTERNAL COMBUSTION ENGINE

(75) Inventors: Eckard Irion, Waldenbuch (DE); Aleksandar Knezevic, Friedrichshafen (DE); Holger Leye, Unterensingen (DE); Mirko Smuk, Waghäusel (DE)

(73) Assignee: Conti Temic Microelectronic GmbH, Nürnberg (DE)

( * ) Notice: Subject to any disclaimer, the term of this patent is extended or adjusted under 35 U.S.C. 154(b) by 0 days.

(21) Appl. No.: 10/230,077

(22) Filed: Aug. 29, 2002

(65) Prior Publication Data

US 2003/0061861 A1 Apr. 3, 2003

(30) Foreign Application Priority Data

Aug. 29, 2001 (DE) ........................................ 101 42 236

(51) Int. Cl.[7] ............................................. G01M 15/00
(52) U.S. Cl. ...................................................... 73/23.31
(58) Field of Search ................................ 73/116, 117.2, 73/117.3, 118.1, 23.31; 60/272–277

(56) References Cited

U.S. PATENT DOCUMENTS 5,540,047 A * 7/1996 Dahlheim et al. ............ 60/274
6,119,448 A * 9/2000 Emmerling et al. .......... 60/274
6,247,303 B1 * 6/2001 Broer et al. .................. 60/274
6,367,320 B1 * 4/2002 Kueper et al. ............. 73/118.1

FOREIGN PATENT DOCUMENTS

DE 199 07 699 C1 11/2000

* cited by examiner

*Primary Examiner*—Max Noori
*Assistant Examiner*—Monica D. Harrison
(74) *Attorney, Agent, or Firm*—Venable LLP; Norman N. Kunitz

(57) ABSTRACT

A method for determining the reducing agent concentration ($NH_3$) in the exhaust-gas flow of an internal combustion engine, using a zeolitic $NH_3$ gas sensor that supplies a base measuring value, which is initially corrected by an offset value and a correction value that depends on the $H_2O$ concentration of the exhaust gas to form an intermediate value. The intermediate value is subsequently corrected by an additional value that depends on the $NO_x$ and $NH_3$ concentration of the exhaust gas. In particular at or above the limits for the operating range, the accuracy of the method increases for one of the following conditions: gas compositions with $NO_x$ concentrations >500 ppm, extremely low $NH_3$ concentrations <20 ppm or high $NH_3$ concentrations >100 ppm.

3 Claims, 4 Drawing Sheets

METHOD FOR DETERMINING THE REDUCING AGENT CONCENTRATION ($NH_3$) IN THE EXHAUST-GAS FLOW OF AN INTERNAL COMBUSTION ENGINE

CROSS-REFERENCE TO RELATED APPLICATION

This application is based on and claims the priority date of German Application No. 101 42 236.9, filed on Aug. 29, 2001, which is incorporated herein by reference.

BACKGROUND OF THE INVENTION

The invention relates to an improved method for determining the reducing agent concentration ($NH_3$) in the exhaust-gas flow of an internal combustion engine.

Nitrogen can be removed from diesel engine exhaust gases by using the selective catalytic reduction (SCR), with ammonia ($NH_3$) as reducing agent. For this purpose, ammonia is carried along in the vehicle either directly or in the form of a compound from which the ammonia is obtained. For the catalytic reduction reaction, ammonia is metered into the engine exhaust gas at a specific ratio to the $NO_x$ content that is momentarily present in the exhaust gas. A stoichiometric $NH_3$—$NO_x$ ratio must exist in order to achieve the maximum possible $NO_x$ conversion. A lower ratio leads to a lower conversion while a higher ratio leads to a so-called "$NH_3$ breakthrough." The optimum use of the nitrogen-removing catalytic converter is achieved with the aid of a zeolitic $NH_3$ gas sensor, which is installed as a control element or as an $NH_3$ breakthrough sensor in the exhaust-gas flow behind the catalytic converter. The $NH_3$—$NO_x$ ratio can thus always be adjusted to the maximum possible $NO_x$ conversion.

The use of a zeolitic $NH_3$ gas sensor requires that a connection be found between the measuring variable and the $NH_3$ concentration to be determined at the sensor. Besides the scaling, this connection is used to compute the compensation of undesirable lateral effects, in particular those to water ($H2_O$) in the form of water vapor in the exhaust gas.

A method for correcting the influence of $H2_O$ on the signal of an $NH_3$ gas sensor is known from German Patent No. DE 199 07 669 C1. The reference suggests determining a so-called zero-value function of the gas sensor, which is then used to correct the measuring values during the continued operation. In order to determine the zero-value function, the gas sensor signal is measured during several different operating phases of the engine while the engine is running, without feeding $NH_3$ to the catalytic converter system. The $H_2O$ concentration in the exhaust gas, the so-called moisture equivalent FÄ (ME), is determined at the same time. The moisture equivalent characterizes the operating state of the engine and is determined from the fuel-mass flow together with the air-mass flow, or from the oxygen partial pressure of the exhaust gas—respectively also in combination with a moisture sensor for determining the $H2_O$ concentration in air that is suctioned in—or with a moisture sensor in the exhaust-gas flow. In all cases, the ascending gradient and the axial section of the zero-value function, which is approximated as a straight line, is determined from the measured values. In order to correct the measured values of the $NH_3$ sensor during operation, the respective zero-value function is determined and the measured sensor value is then corrected accordingly.

However, the known method has a number of disadvantages.

The delayed response (response threshold) of the $NH_3$ sensor for low $NH_3$ concentrations is not taken into account. In the same way, the influence of the $NO_x$ gas components on the response threshold and the $NH_3$ sensitivity are not taken into account. When determining the zero-value function, a linear approximation of the dependence between measured value (Cp) and $NH_3$ concentration is made, which provides acceptable results only for $NH_3$ concentrations up to approximately 50 ppm. The adsorption and conversion behavior of the $NH_3$ sensor, which leads to a distortion of the gas composition arriving at the sensor, is also not taken into consideration.

SUMMARY OF THE INVENTION

Thus, it is the object of the invention to provide a method for correcting the signal from a $NH_3$ sensor, which method provides an exact value for the measured $NH_3$ concentration, even with low $NH_3$ concentrations. At the same time, the method takes into account the adsorption behavior and the conversion behavior of the $NH_3$ sensor.

The above object generally is achieved according to the invention by a method for determining the reducing agent concentration ($NH_3$) in the exhaust-gas flow of an internal combustion engine with a (zeolitic) $NH_3$ gas sensor that supplies a base measuring value, wherein the base measuring value is initially corrected by an offset value and by a correction value that depends on the $H_2O$ concentration of the exhaust gas to form an intermediate value. Following this, the intermediate value is corrected by an additional value that depends on the $NO_x$ concentration of the exhaust gas to obtain a corrected $NH_3$ measuring value.

The values for the dependence of the measured values on the $NO_x$ concentration and the $NH_3$ concentration are recorded in a 2-dimensional table.

The two adjacent columns in the table, which best match the given $NO_x$ concentration, are selected to determine the $NH_3$ concentration. Following that, the line that best matches the first intermediate value is determined in the first selected column and the final measured value is then determined through interpolation, initially between the columns and then between the lines.

The invention is explained in further detail in the following with the aid of embodiments and Figures.

DESCRIPTION OF THE PREFERRED EMBODIMENTS

Figure 4:
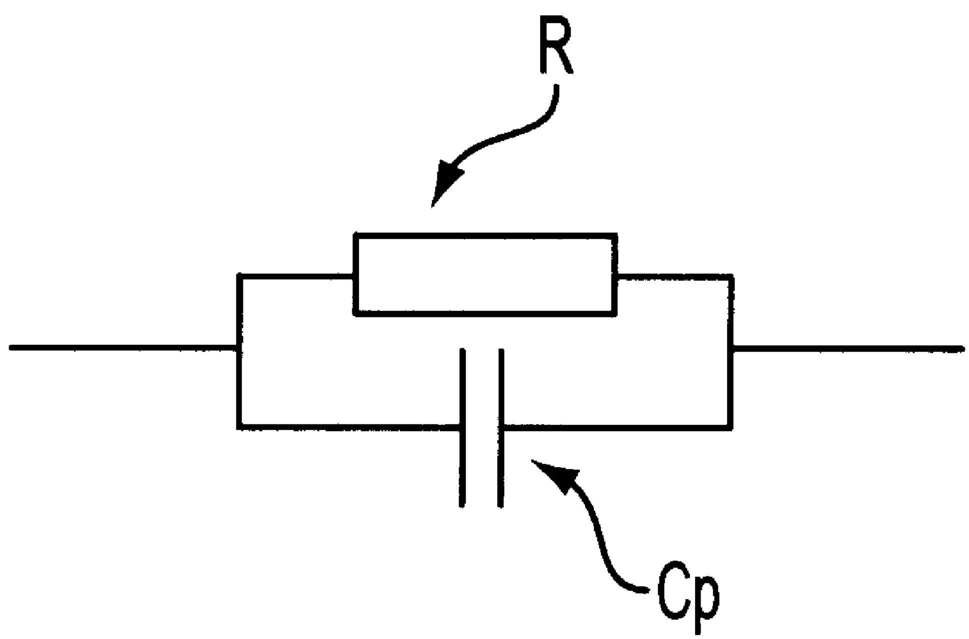
FIG. 4 shows a simplified equivalent circuit for the sensor.

An extremely simplified sensor model was used and the following assumptions were made for the observations based on the initially mentioned prior art:

The parallel capacitance $C_p$ in an equivalent circuit diagram for the sensor shown in FIG. 4 characterizes the $NH_3$ concentration. A linear dependence exists between the $NH_3$ concentration and the parallel capacitance $C_p$ in the equivalent circuit diagram for the sensor. The equivalent circuit diagram shows that $H_2O$ exerts a linear influence on the parallel capacitance $C_p$, independent of the $NH_3$ concentration. Nitrogen oxides $NO_x$ do not influence the sensor signal and no interaction occurs between the gas components.

Thus, it follows for the measured capacitance of the sensor element:

$$C_p = C_{pO} + v_{NH3} \cdot NH_3 + v_{H2O} \cdot H_2O \quad (1)$$

$C_p$: total capacitance of the sensor element $C_{pO}$: basic capacitance $V_{NH3}$: factor $NH_3$ influence $V_{H2O}$: factor $H2_O$ influence $NH_3$: concentration $NH_3$ $H_2O$: concentration $H_2O$ Relative to the searched-for $NH_3$ concentration and the measuring variable $C_p$, the following results:

$$NH_{3model} = v'_{NH3} \cdot (C_p - C_pO) + v'_{H2O} \cdot H_2O \quad (2)$$

The model has a simple formulation and uses only 3 (calibration) parameters along with 1 measured value.

The disadvantages of this correction method based on this model are as follows:

Delayed response (response threshold) for low $NH_3$ concentrations is not taken into account.

Influence of the $NO_x$ gas components on the response threshold and the $NH_3$ sensitivity are not taken into account.

Experimentally determined, non-linear dependence between measured variable ($C_p$) and $NH_3$ concentration is approximated linearly, which supplies acceptable results only for $NH_3$ concentrations up to approximately 50 ppm.

Adsorption and conversion behavior of the sensor/packing that leads to a distortion of the gas composition arriving at the sensor are not taken into account.

The correction method based on this simple model does not meet the requirements for the exhaust gas system and the environmental conditions to be expected there with respect to measuring accuracy. The measuring error consists of three parts: the errors caused by the sensor, the model errors and the errors in the evaluation electronics (digitizing errors, signal noise, . . . ).

$$F\_sought = F\_sensor + F\_model + F\_electronics \quad (3)$$

In particular the influence of the lateral sensitivities caused by changes in the environmental conditions can be improved noticeably by reducing the model error.

The new method is based on the following findings:

In the >20 ppm range, a nearly logarithmic connection exists between the $NH_3$ concentration and $C_p$.

With extremely low concentrations (<20 ppm), the increase in the capacitance is delayed; the delay is even greater if $NO_x$ is present.

Even with higher $NH_3$ concentrations, there is a reduced sensitivity relative to $NH_3$ in the presence of nitrogen oxides.

Nitrogen oxides significantly influence the measuring results (interaction, side effect) only if $NH_3$ is present.

The influence of water on the measuring result without interaction to the $NH_3$ effect and in the range of 1–8 vol % $H2_O$ is linear.

Thus, without taking into account the $NO_x$ effects it follows that:

$$C_p = C_{p0} + v^*_{NH3} \cdot \log\left(\frac{NH_3}{s_{NH3}} + 1\right) + v_{H2O} \cdot H_20 \quad (4)$$

$C_p$: total capacitance of the sensor element $C_{pO}$: basic capacitance $V_{NH3}$: factor $NH_3$ influence (sensitivity)

Figure 1:
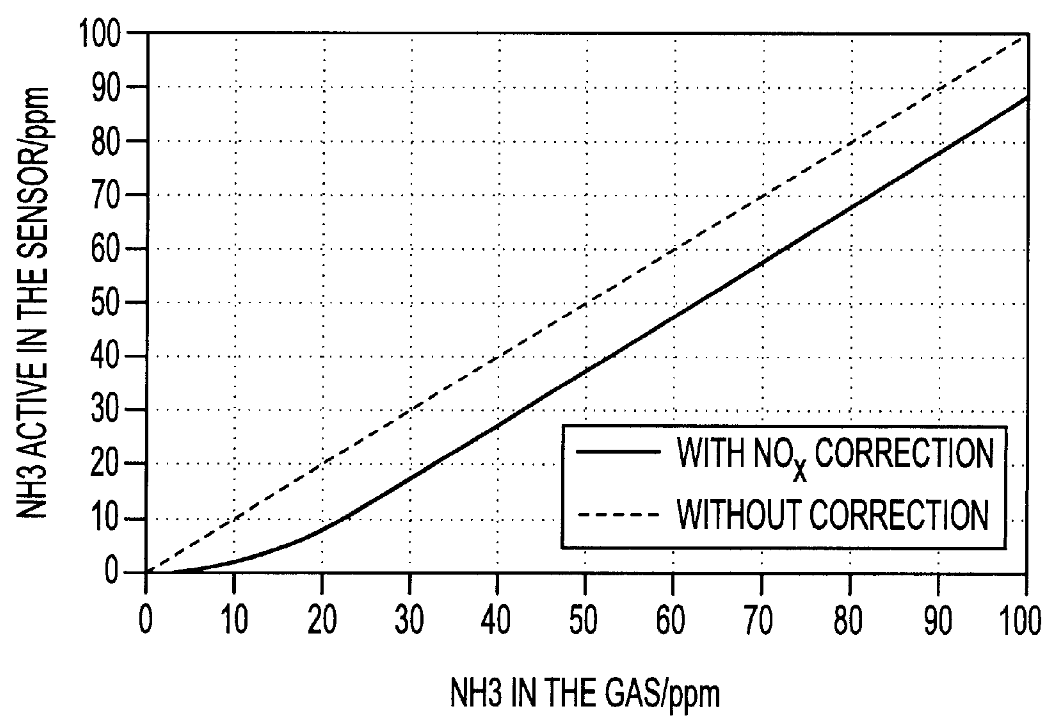
FIG. 1 shows the $NO_x$ correction of the $NH_3$ concentration at the sensor.

$NH_3$: concentration $NH_3$ $S_{NH3}$: factor for characterizing the $NH_3$ influence $V_{H2O}$: factor for characterizing the $H_2O$ influence $H_2O$: concentration $H_2O$ However, due to the presence of nitrogen oxides, catalytic surfaces, adsorption and decomposition reactions, a portion of the $NH_3$ molecules already react at the sensor and cannot be detected by this sensor. FIG. 1 shows an example of the difference between $NH_3$ concentration in the gas and the concentration that contributes to the measuring effect in the sensor.

To compensate for this influence, the $NH_3$ term from equation (4) is replaced with the corrected one:

$$NH_{3sensor} = \frac{NH_3^p}{NH_3^p + \Delta} NH_3 = \frac{NH_3^{p+1}}{NH_3^p + \Delta} \quad (5)$$

p: influence parameter $NO_x$ (width of transition zone)

$NH_3$: $NH_3$ concentration in the gas $NH_{3sensor}$: sensor-effective $NH_3$ concentration With the following dependence:

$$\Delta = \alpha_{NO} + v_{NO} \cdot NO \quad (6)$$

$\alpha_{NO}$: influencing parameters of $NO_x$-independent processes (adsorption, catalytic conversion)

$v_{NO}$: influencing parameters $NO_x$

NO: concentration of nitrogen oxides $NO_x$

In the borderline case $\Delta \to O$ or with extremely high $NH_3$ concentrations, equation (5) changes over to $NH_{3corr} = NH_3$. Based on equations (4), (5) and (6), it follows for the corrected total capacitance Cp:

$$C_p = C_{p0} + v_{NH3} \cdot \log\left(\frac{NH_3^{p+1} \cdot s_{NH3}}{NH_3^p + \alpha_{NO} + v_{NO} \cdot NO} + 1\right) + v_{H20} \cdot H_20 \quad (7)$$

Figure 2:
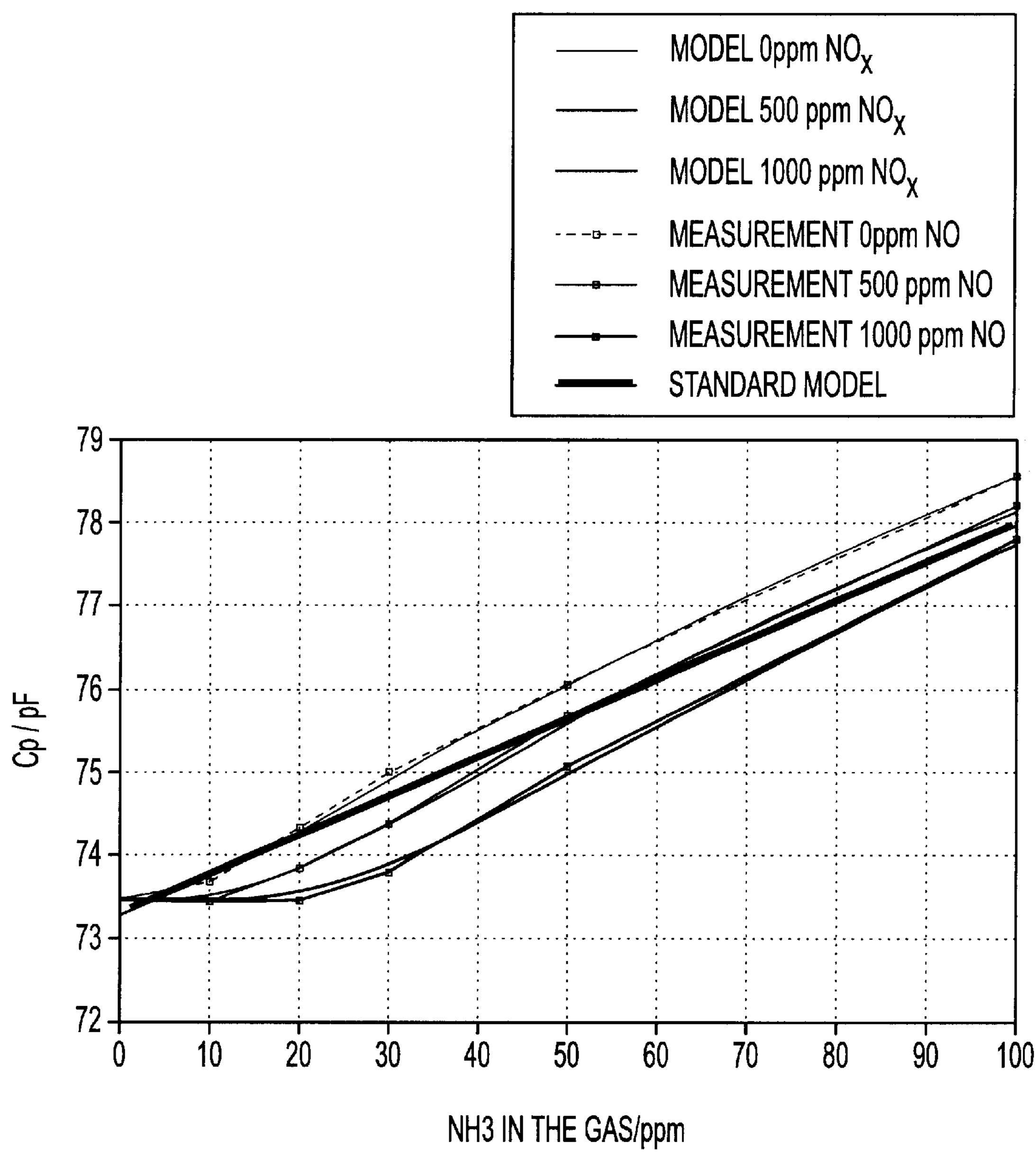
FIG. 2 shows comparison models for the measuring data.

The advantages of the new method become clear even in the typical, narrow operating range of the $NH_3$ sensor with maximum 100 ppm $NH_3$ and up to 1000 ppm NO. It is easy to see in FIG. 2 that a linear approximation to the measuring results would provide noticeably poorer results.

The following maximum error therefore can be expected for a use range of:

1–8 vol % $H2_O$ and

0–100 ppm $NH_3$, as well as

0/500/1000 ppm $NO_x$,

| ΔCp/Pf | prior art: | invention: |
|---|---|---|
| 0 ppm NO | 0.53 | 0.05 |
| 500 ppm NO | 0.37 | 0.09 |
| 1000 ppm NO | 0.87 | 0.11 |
| maximum | 0.87 (18 ppm $NH_3$) | 0.11 (2 ppm $NH_3$) |

Further taking into account the fact that measuring errors stemming from the measuring instruments in use and the configuration also enter into this error, an improvement by at least a factor of 8 can be assumed, even for the limited operating range.

Figure 3:
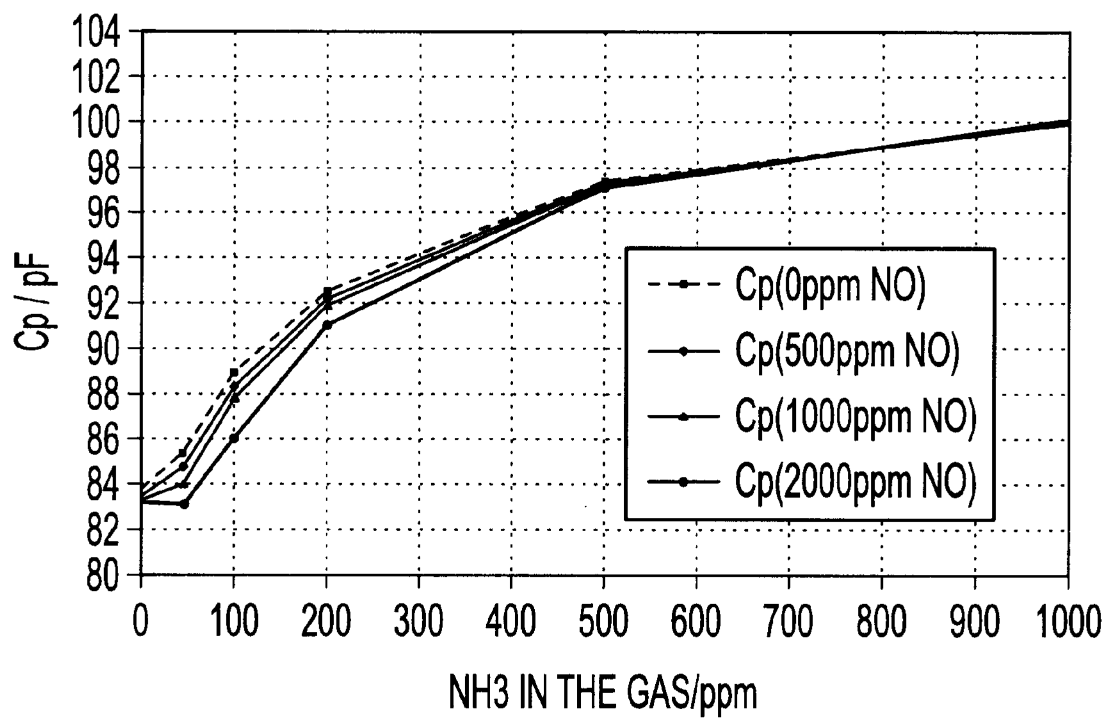
FIG. 3 shows the $NH_3$ sensor response behavior in the expanded measuring range.

In particular at/above the limits of the operating range and given one of following conditions gas compositions with $NO_x$ concentrations >500 ppm extremely low $NH_3$ concentrations <20 ppm high $NH_3$ concentrations >100 ppm the advance in the prediction accuracy increases even further. This is shown clearly with the measuring results shown in FIG. 3 for the expanded range.

As a result of the noticeable increase in the complexity of the model, the equation (7) unfortunately can no longer be algebraically transposed to $NH_3$. Furthermore, the microcontroller, used so far for the signal processing, would no longer be able to perform the necessary calculations during the time available for this.

The alternative of using a complete tabulation is not practical since a large amount of memory is required as a result of the 3 influencing variables. If the equation (7) is divided into the three components $$C_p = C_pO + C_p(NH_3NO_x) + C_p(H_2O), \quad (8)$$

it becomes obvious that the no-load capacitance $Cp_O$ as well as the $H_2O$ term can be eliminated through subtraction. The 2 parameters required for this are stored in the non-volatile memory of the electronics. The $H_2O$ concentration is obtained from external data. The remaining dependencies on $NH_3$ and NO concentrations are stored, as shown in Table 1, in a 2-dimensional table, a so-called lateral sensitivity table.

TABLE 1 lateral sensitivity table

| ΔCp/pF | $NO_x$ = 0 ppm | $NO_x$ = 100 ppm | $NO_x$ = 200 ppm |
|---|---|---|---|
| NH3 = 0 ppm | 0.0 | 0.0 | 0.0 |
| NH3 = 20 ppm | 1.1 | 1.0 | 0.9 |
| NH3 = 40 ppm | 1.6 | 1.5 | 1.4 |
| NH3 = 60 ppm | 2.0 | 1.9 | 1.8 |
| ... | ... | ... | ... |

The algorithm effect on the total operational sequence occurs rather early:

Sensor element production;

Scanning of corner data based on the framework conditions for the algorithm and measuring of the sensors at these points;

Regression of model parameters by means of previously determined measuring data;

Determination of 2 parameters for $C_pO$ and $H_2O$

Computation of the above-mentioned value tables by means of an algorithm and the framework conditions for the area of use;

Storage of characteristic data and the table in the microcontroller memory;

Deployment of the sensor by using an interpolation algorithm.

The sensor electronics determines the $NH_3$ concentration from the measuring value $C_p$ with the following steps:

Subtraction of the no-load capacitance from the measured value with stored parameter $C_pO$;

Subtraction of the $H_2O$ influence with $H_2O$ parameter and supplied $H_2O$ concentration;

The two adjacent columns in the lateral sensitivity table with the closest match to the predetermined $NO_x$ concentration are selected;

By using a search algorithm (e.g. bisection method), the line that most closely matches the converted measuring value in the first selected column is determined;

Through linear interpolation between initially the columns and then the lines, the $NH_3$ value is determined through projection onto the $NH_3$ line association.

Output of the $NH_3$ concentration that is determined.

By using these steps, the complete algorithm can be realized through elementary operations such as addition and multiplication. The error resulting from the linear interpolation can be kept extremely low through a suitable selection of the support or restart points in the table. It is advantageous if a higher support point density is selected in regions of high non-linearity.

The invention now being fully described, it will be apparent to one of ordinary skill in the art that many changes and modifications can be made thereto without departing from the spirit or scope of the invention as set forth herein.

What is claimed is:

1. A method for determining the reducing agent concentration ($NH_3$) in the exhaust-gas flow of an internal combustion engine with an $NH_3$ gas sensor that supplies a base measuring value, comprising initially correcting the base measuring value by an offset value and a correction value that depends on the $H_2O$ concentration in the exhaust gas to obtain an intermediate value; and subsequently changing the intermediate value with the aid of the $NO_x$ concentration in the exhaust gas to provide a corrected $NH_3$ measuring value.

2. The method according to claim 1, including storing the values for the dependence on the $NO_x$ and the $NH_3$ concentrations in a 2-dimensional table.

3. The method according to claim 2, wherein the step of changing includes:

selecting the two adjacent columns in the table that best match the given $NO_x$ concentration;

determining the line in the first selected column that best matches the first intermediate value; and determining the final measuring value through interpolation, initially between the columns and then between the lines.

* * * * *